United States Patent
Tabacchi

(10) Patent No.: US 8,061,836 B2
(45) Date of Patent: Nov. 22, 2011

(54) METHOD OF MANUFACTURING SPECTACLES OF THE SINGLE-LENS, WRAP-AROUND TYPE AND SPECTACLES PRODUCED BY THE METHOD

(75) Inventor: Massimiliano Tabacchi, Padua (IT)

(73) Assignee: SAFILO Societa Azionaria Fabbrica Lavorazione Occhiali S.p.A., Pieve Di Cadore BL (IT)

( * ) Notice: Subject to any disclaimer, the term of this patent is extended or adjusted under 35 U.S.C. 154(b) by 25 days.

(21) Appl. No.: 12/303,322

(22) PCT Filed: Jun. 6, 2006

(86) PCT No.: PCT/IT2006/000422
§ 371 (c)(1),
(2), (4) Date: Jun. 18, 2009

(87) PCT Pub. No.: WO2007/141812
PCT Pub. Date: Dec. 13, 2007

(65) Prior Publication Data
US 2009/0323016 A1      Dec. 31, 2009

(51) Int. Cl.
*G02C 1/02*     (2006.01)
(52) U.S. Cl. ............ 351/110; 351/41; 351/178; 264/1.1
(58) Field of Classification Search .............. 351/41, 351/44, 45, 154, 159, 177, 187, 178; 264/1.1, 264/1.32, 2.7
See application file for complete search history.

(56) References Cited

U.S. PATENT DOCUMENTS

| 2,179,286 A |   | 1/1939 | English |
| D208,502 S | * | 9/1967 | Halpern et al. .............. D16/314 |
| 3,526,449 A |   | 9/1970 | Bolle et al. |
| 3,705,760 A |   | 12/1972 | Langendorfer et al. |
| 6,082,857 A | * | 7/2000 | Lockhart ....................... 351/178 |

FOREIGN PATENT DOCUMENTS

| DE | 20 2004 002 495 |   | 4/2004 |
| GB | 2052087 | A | 1/1981 |
| GB | 2218824 | A | 11/1989 |
| GB | 2 252 637 |   | 8/1992 |

OTHER PUBLICATIONS

Jan. 28, 2011 European Office Action (EP Appln. No. 06 766 312.0 - 2204) reporting two new references.

* cited by examiner

*Primary Examiner* — Huy K Mai
(74) *Attorney, Agent, or Firm* — Volpe and Koenig, P.C.

(57) ABSTRACT

In a method of manufacturing spectacles of the type which does not have a lens-holding frame and which has a single, wrap-around front lens structure that can extend laterally beyond the main visual regions, and which also has respective arms for the lateral support of the spectacles, predominant portions of the respective lateral arms of the spectacles are produced integrally with the front lens structure by a process for the forming of plastics material with which a semi-finished lens is produced, so that the spectacles are consequently produced in a single piece.

14 Claims, 4 Drawing Sheets

METHOD OF MANUFACTURING SPECTACLES OF THE SINGLE-LENS, WRAP-AROUND TYPE AND SPECTACLES PRODUCED BY THE METHOD

A method of manufacturing spectacles of the single-lens, wrap-around type and spectacles produced by the method

TECHNICAL FIELD

The present invention relates to a method of manufacturing spectacles of the single-lens, wrap-around type, according to the preamble to the main claim.

BACKGROUND ART

The invention relates particularly to the specific field of protective spectacles such as those that are designed for protection against sunlight and are commonly known by the term "goggles", that is, spectacles having lenses with a marked degree of front and side wrap-around. More particularly, these spectacles are distinguished by the fact that they do not have a front lens-holding frame but have a single lens structure with a high degree of wrap-around, extending from the main visual regions to beyond the opposed and respective side regions. Today, spectacles of these types, which are generally designed and intended for sports activities, have taken on a strong stylistic character and have become widely used amongst the public even as fashion accessories with a high degree of aesthetic impact. In this field, it is known to manufacture goggles by the preliminary production of the wrap-around lens structure which is then intended to be articulated to the lateral supporting arms which are produced separately and distinctly from the lens.

DESCRIPTION OF THE INVENTION

The main object of the invention is to provide single-lens wrap-around spectacles in which the production process is simplified and the components used are more easily assembled.

Yet another object is to produce wrap-around lens structures in which the marked lateral curvature is accompanied by the maintenance of optimal optical properties for correct vision through the lens structure.

These and yet further objects which will become clear from the following description are achieved by the invention by means of a method of manufacturing spectacles implemented in accordance with the appended claims.

BRIEF DESCRIPTION OF THE DRAWINGS

The characteristics and the advantages of the invention will become clearer from the following detailed description of some preferred embodiments thereof which are described by way of non-limiting example with reference to the appended drawings, in which.

PREFERRED METHOD OF IMPLEMENTING THE INVENTION

Figure 1:
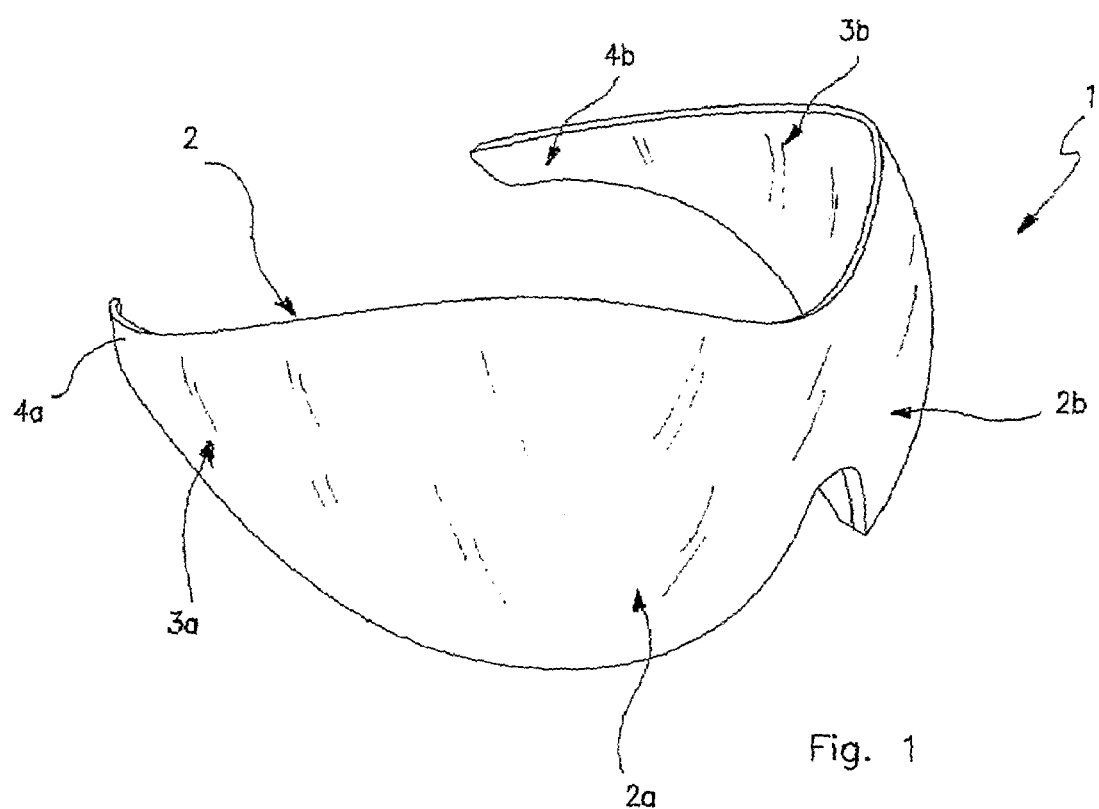
FIG. 1 is a perspective view of a first embodiment of spectacles produced in accordance with the method of the invention.

With reference initially to FIGS. 1 to 4, a first embodiment of spectacles produced in accordance with the method of manufacture of the present invention is generally indicated 1.

The spectacles 1 are of the type commonly know by the term "goggles", that is, they comprise a single front lens structure 2 which has a marked degree of wrap-around and in which the main visual regions, indicated 2a and 2b, respectively, are incorporated. Each of the main visual regions 2a, 2b is then extended laterally by a respective lateral region 3a, 3b which is arranged adjacent the temporal region of the head (when the spectacles are being worn), and which extends laterally towards the respective arms 4a, 4b for supporting the spectacles on the ear regions of the head.

Figure 3:
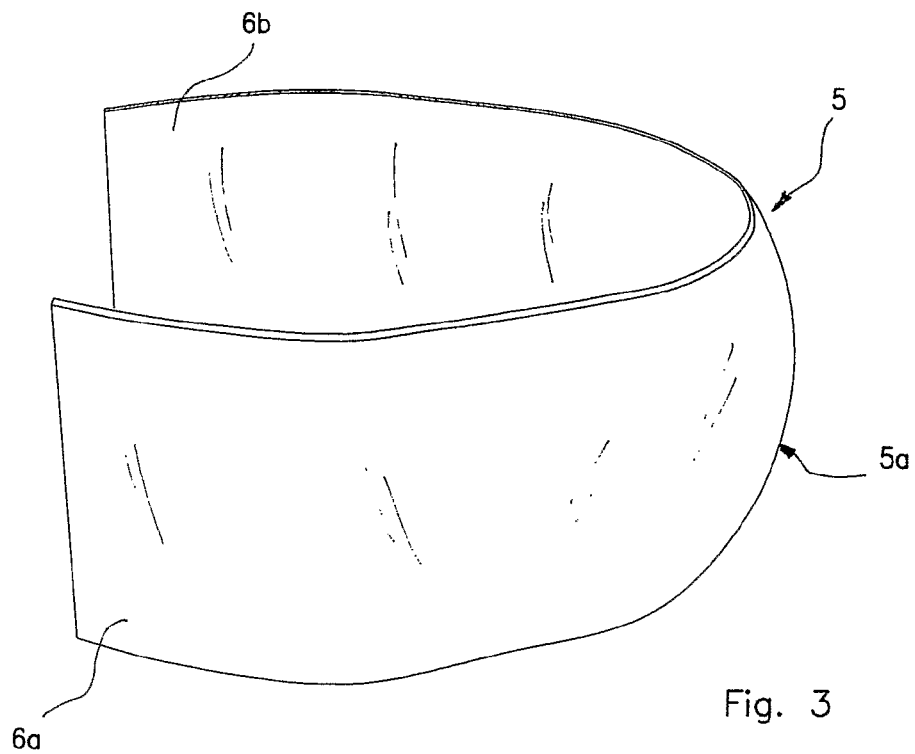
FIGS. 3 and 4 are perspective views of a semi-finished lens of the spectacles of the preceding drawings, produced in a step of the method of the invention.
Figure 4:
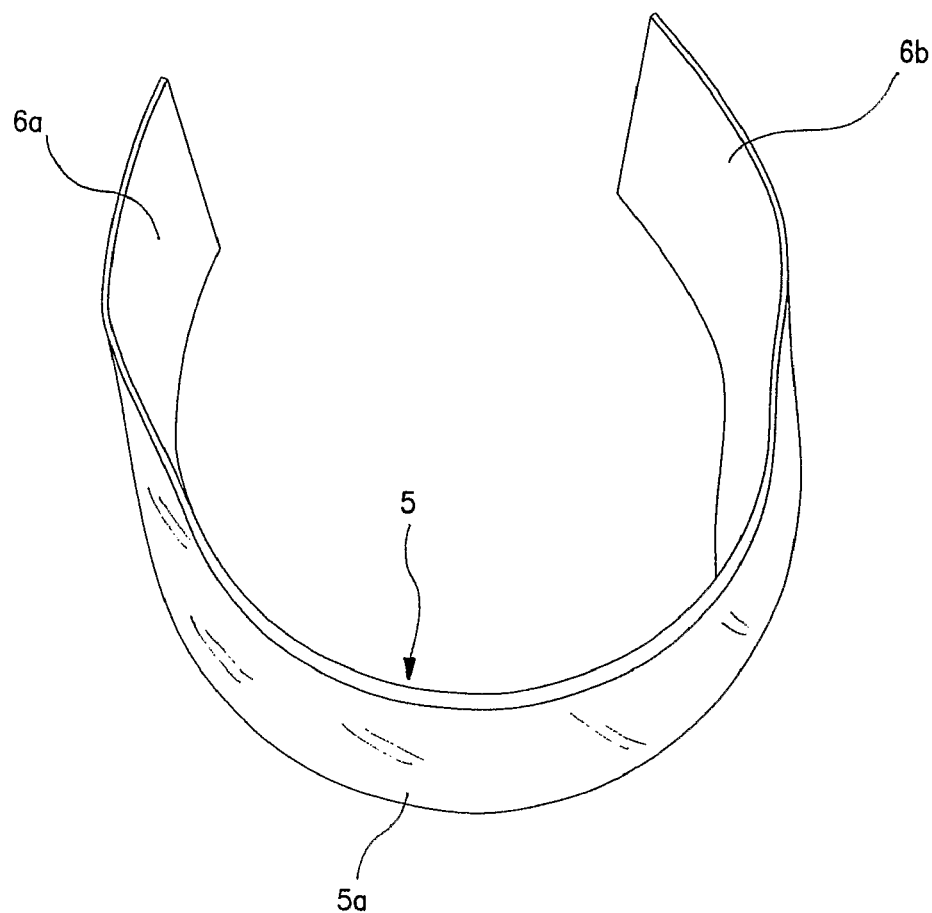

Moreover, the spectacles 1 have no lens-holding frame and are produced by a method of manufacture in which a first step provides for the production of a semi-finished lens 5 shown in FIGS. 3 and 4.

The semi-finished lens 5 is advantageously produced by the forming of a plastics material by an injection process or alternatively by casting. Further techniques that can be used to produce the semi-finished lens 5 are thermo-forming and compression moulding.

In thermo-forming, a sheet of heated plastics material is forced against the walls of a mould by suction due to a vacuum or by means of compressed air.

In compression moulding, the plastics material adopts the shape of the mould as a result of a mechanical pressure (mating between matrices). The material may be inserted in the heated mould in the intermediate form of a sheet of plastics material. For thermo-setting plastics materials, it is also known to insert the material in the mould in powder form and to bring about cross-linking and forming thereof by pressure and heating.

A front portion 5a which has larger dimensions than the preselected lens structure 2 of the finished spectacles is identified in the semi-finished lens 5, as are respective lateral extensions 6a, 6b which extend integrally from the portion 5a and the longitudinal extent of which is equal to or greater than a preselected average length of conventional arms for spectacle frames. The respective lateral arms 4a, 4b of the spectacles are thus produced integrally with the front lens structure 2 by forming of the plastics material of which the semi-finished lens 5 is made, the spectacles 1 consequently being produced entirely in a single piece.

Figure 2:
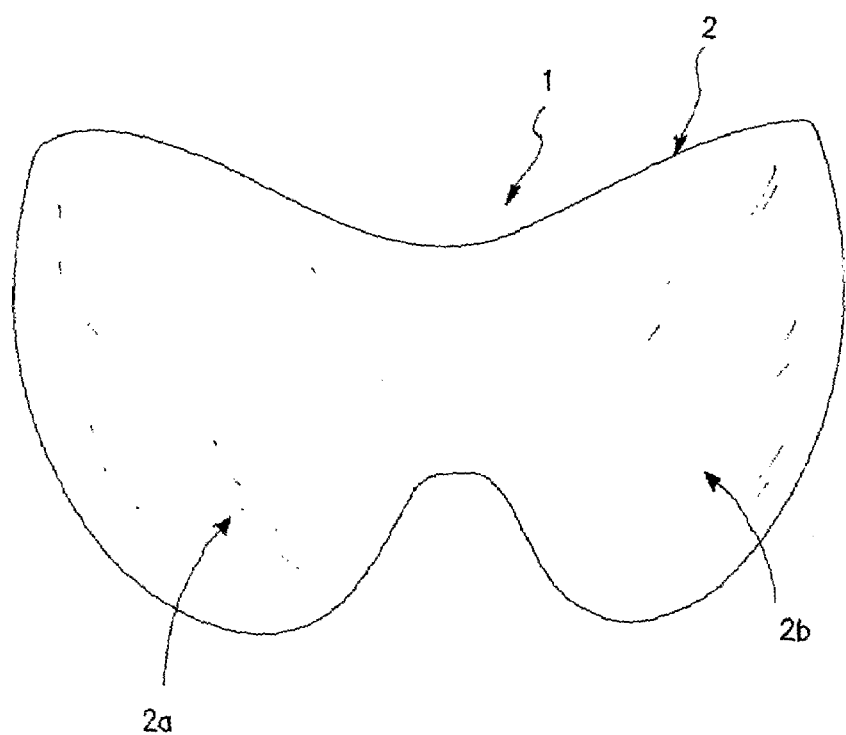
FIG. 2 is a front view of the spectacles of FIG. 1.
Figure 2A:
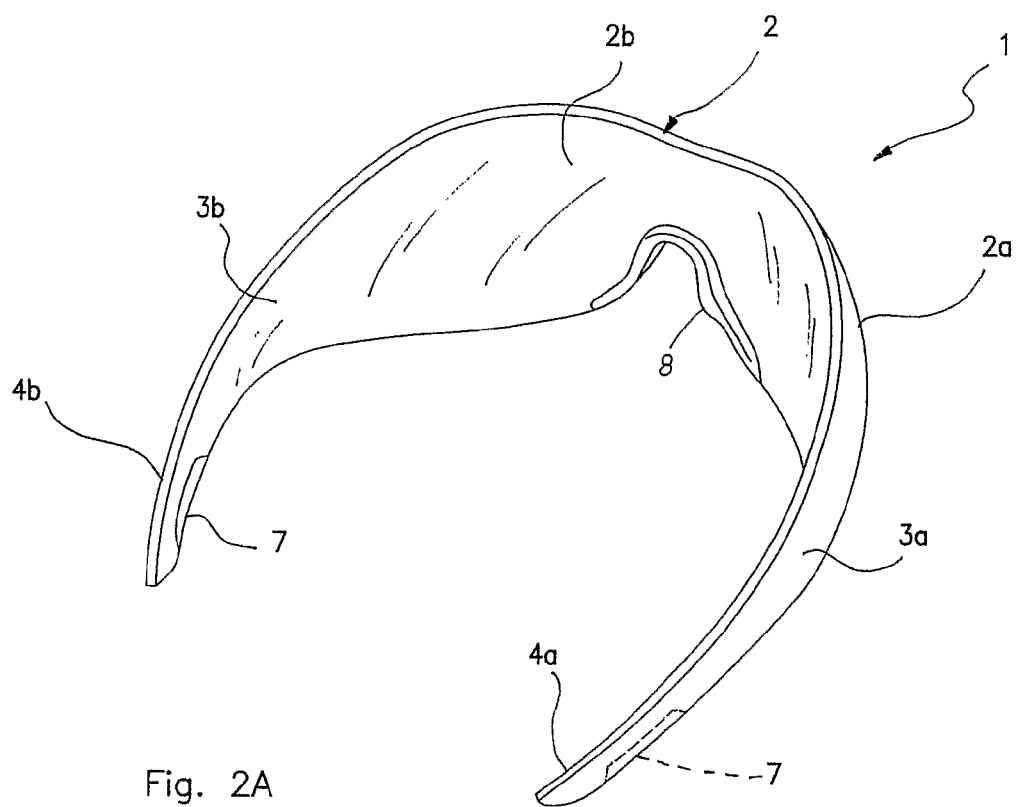
FIG. 2A is a further perspective view of the spectacles of the previous drawings.

A subsequent step of the method of the invention provides for the semi-finished lens 5 to be subjected to shaping machining with the removal of material, during which both the arms 4a, 4b and the lens structure 2 are shaped to the final shape in accordance with the preselected style as shown in FIGS. 1 and 2. In this step, the arms 4a, 4b are shaped to the preselected length suitable for ensuring the support of the spectacles on the ears and the front lens structure 2 is trimmed to the desired shape.

The spectacles are also provided with elements 7 which are made of soft material and are fitted on the respective arms 4a, 4b in the regions that rest on the ears, in the end portions of the arms. These elements 7 are preferably fixed to the inner side of the lens structure to permit support with comfortable contact. Alternatively, the ear-rest elements 7 may be produced in the form of inserts or shells suitably fitted on the end portions of the arms.

Similarly, a nose-rest element 8 is fitted on the lens structure 2 in the central region connecting the main visual regions 2a, 2b.

Figure 5:
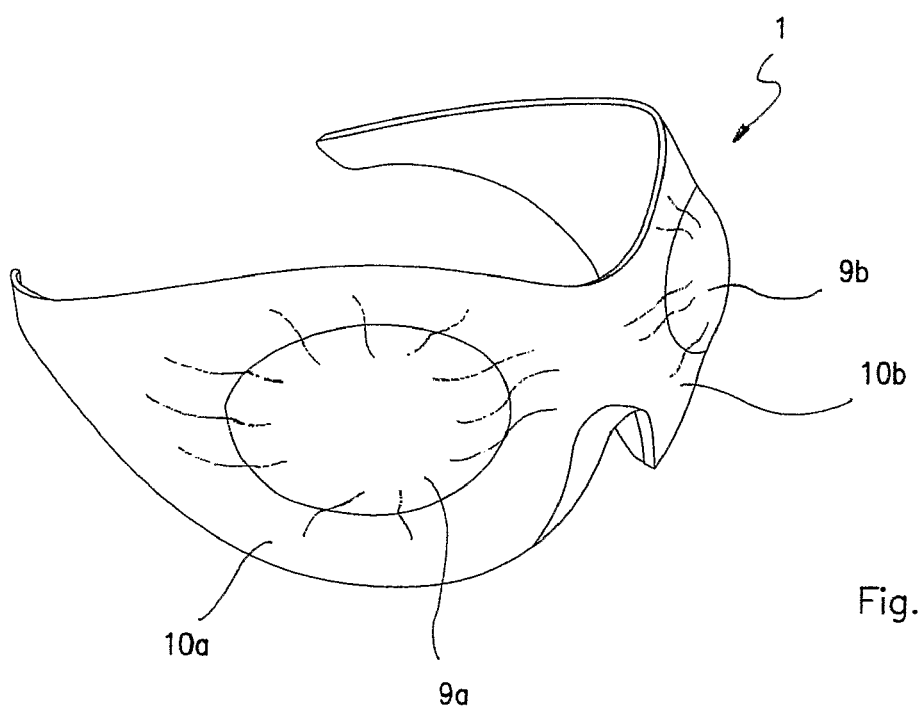
FIG. 5 is a perspective view of a second embodiment of the method of the invention.
Figure 6:
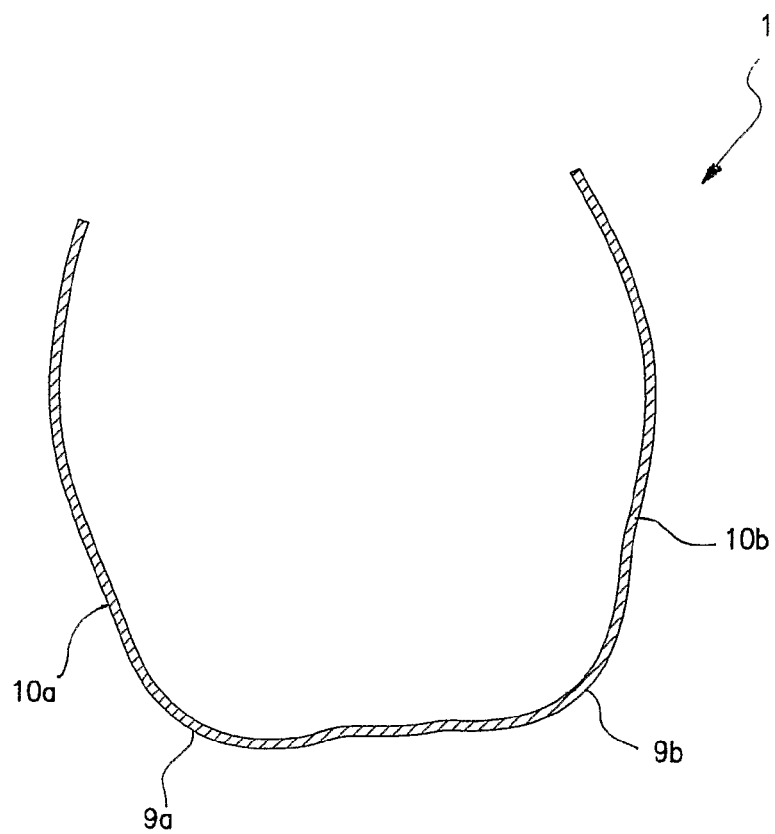
FIG. 6 is a schematic view, sectioned in a transverse median plane, of the spectacles of FIG. 5 produced in accordance with the method of the invention.
Figure 7:
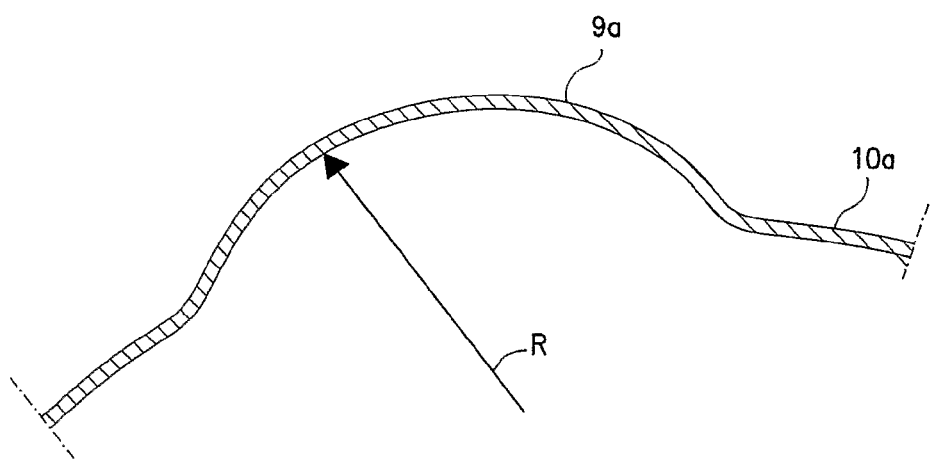
FIG. 7 shows a detail of FIG. 6 in section and on an enlarged scale.

According to a further characteristic of the invention, in each of the main visual regions 2a, 2b, the front lens structure 2 has a curvature of the opposed lens surfaces which is greater than the curvature in an adjacent region extending at the periphery of the corresponding main visual region. The above-mentioned central visual regions that are characterized by marked curvature are indicated 9a and 9b and are such as to be displaced away from the face in comparison with the corresponding adjacent regions when the spectacles are being worn. In the latter regions, which are indicated 10a, 10b in FIG. 5, the basic curvature of the lens structure 2 may also be maintained, the transition from these regions to the corresponding central regions taking place by a gradual change in the radius of curvature, as shown in FIG. 5.

The central regions 9a, 9b with marked curvature may advantageously have spherical surface profiles and may also be produced distinctly and separately from one another. It should be understood that the central regions and the corresponding adjacent regions may have different surface shapes but the shape described represents a preferred choice.

For example, the central regions with marked curvature may be constituted by portions of spheres, cylinders, or toroids. Similarly, the adjacent regions may have, for example, spherical, cylindrical or toric shapes. The shape of the central regions with marked curvature may differ from that selected for the adjacent regions.

Moreover, the outlines of the central regions with marked curvature, meaning the "weld lines" between each central region and the main lens body, which are represented herein by way of non-limiting example by circular outlines, may adopt different shapes (for example, an oval or elliptical shape) according to stylistic selections and the aesthetic effects to be achieved.

In any case, both the central regions with marked curvature and the remaining adjacent regions are produced in a manner such as to minimize undesired prismatic effects (or prismatic optical properties) which, if they were significant, could lead to defects in refraction such as distortions and/or discontinuities of the image transmitted, with consequent discomfort for the user due to fatigue or difficulty in seeing.

The magnitude of the prismatic effects is connected both with the thickness and with the curvature of the lenses. The greater the thickness and/or the curvature are, the greater is the magnitude of the prismatic optical properties.

The prismatic effects are eliminated (when necessary, that is, with considerable lens thicknesses and/or curvatures) in all of the regions of the lens (and hence not solely in the central regions with marked curvature) by means of known constructional criteria.

These criteria are based on differentiation between the curvature of the external surface and the curvature of the internal surface of a given region of a lens. The differentiation of the surfaces relates both to the values of the respective radii of curvature and to the positions of the respective centres of curvature (non-concentric surfaces with so-called "optical decentralization" or "optical correction"). This differentiation generally results in variation of the thickness of the lens from one point to another; basically, this controlled variation counteracts the undesired prismatic optical effects, cancelling them out or bringing them to insignificant values. The invention thus achieves the objectives proposed, affording many advantages over known solutions.

A first main advantage lies in the fact that the method of manufacture of the invention simplifies the production process, enabling the basic structure of the single wrap-around lens to be produced by means of a single machining session, for example, with the use of a single numerically controlled machine tool, without the need for retooling thereof.

Another advantage is connected with the reduction in the number of parts used in the assembly; in particular, owing to the fact that no fixing means are required between the lens and the arms, the number of components used in the manufacturing process is reduced.

Another advantage lies in the considerable and pleasing aesthetic impact which is emphasized by the presence of transparent surfaces which are also present in the lateral portions of the support arms, bearing in mind that, in wrap-around spectacles of conventional shape, the transparent portion extends from the front portion as far as a limited lateral portion in the temple region.

Yet another advantage is that the provision of central visual regions with marked curvature ensures a sufficient and comfortable distance of the spectacles from the face where the high degree of wrap-around of the lens could create problems in the wearability of the spectacles by interfering with the face.

The invention claimed is:

1. A method of manufacturing spectacles of the type which does not have a lens-holding frame and which has a single, wrap-around front lens structure that can extend laterally beyond the main visual regions, and which also has respective arms for the lateral support of the spectacles, predominant portions of the respective lateral arms of the spectacles are produced integrally with the front lens structure by a process for the forming of plastics material with which a semi-finished lens is produced, so that the spectacles are consequently produced in a single piece, wherein by the forming step the spectacles comprise a single front lens structure having a marked degree of wrap-around and in which the main visual regions with the optical properties are incorporated and in that, after the forming step, a step is provided for shaping the semi-finished lens by machining with the removal of material, during which the arms and the single front lens structure are shaped to the final shape in accordance with a preselected style.

2. A method according to claim 1 wherein the arms have a longitudinal extent in the semi-finished lens such that they can be shaped to a preselected length suitable for ensuring the support of the spectacles on the ear region of the head.

3. A method according to claim 1 wherein a step is provided for fitting respective elements made of soft material on the end portions of the arms in the regions which rest on the ear regions of the head.

4. A method according to claim 3 wherein the ear-rest elements are fixed in the region of the end portions of the arms, on the inner side of the lens structure.

5. A method according to claim 1 wherein step is provided for fitting a nose-rest element on the single front lens.

6. A method according to claim 1 wherein in the main visual regions, the single lens structure has respective central regions with curvature of the opposite lens surfaces that is greater than the curvature in respective adjacent regions extending at the peripheries of the corresponding central visual regions so that the lens portion of each of the central visual regions is displaced away from the face in comparison with the corresponding adjacent lateral region when the spectacles are being worn.

7. A method according to claim 6 wherein the central visual regions with marked curvature have spherical, cylindrical, or toroidal surface profiles.

8. A method according to claim 6 wherein the transition from the central visual region to the adjacent region takes place by a gradual change in the radii of curvature of the respective regions.

9. A method according to claim 6 wherein the central visual regions with greater curvature are distinct and separate from one another.

10. A method according to claim 6 wherein the forming process is performed by injection of plastics material.

11. A method according to claim 1 wherein the forming process is performed by casting of plastics material.

12. A method according to claim 1 wherein the forming process is performed by thermo-forming of plastics material.

13. A method according to claim 1 wherein the forming process is performed by compression-moulding of plastics material.

14. Spectacles of the type which does not have a lens-holding frame and which has a single, wrap-around front lens structure that can extend laterally beyond the main visual regions and which also has respective arms for the lateral support of the spectacles, the spectacles being produced in accordance with the method of manufacture of any one of the preceding claims.

* * * * *

UNITED STATES PATENT AND TRADEMARK OFFICE
CERTIFICATE OF CORRECTION

| | | |
|---|---|---|
| PATENT NO. | : 8,061,836 B2 | Page 1 of 1 |
| APPLICATION NO. | : 12/303322 | |
| DATED | : November 22, 2011 | |
| INVENTOR(S) | : Massimilliano Tabacchi | |

It is certified that error appears in the above-identified patent and that said Letters Patent is hereby corrected as shown below:

In Claim 1, column 4, line 45, replace "by machining" with --by machine--.

Signed and Sealed this
Seventeenth Day of April, 2012

David J. Kappos
*Director of the United States Patent and Trademark Office*